United States Patent [19]

Sims

[11] Patent Number: 4,638,796

[45] Date of Patent: Jan. 27, 1987

[54] METHOD OF DRESSING WOUNDS

[75] Inventor: Calvin L. Sims, Richardson, Tex.

[73] Assignee: Winfield Laboratories, Inc., Richardson, Tex.

[21] Appl. No.: 621,074

[22] Filed: Jun. 15, 1984

Related U.S. Application Data

[63] Continuation of Ser. No. 352,117, Feb. 25, 1982, abandoned.

[51] Int. Cl.$^4$ .............................................. A61F 13/00
[52] U.S. Cl. ..................................... 128/155; 128/156
[58] Field of Search ................................. 128/155–156

[56] References Cited

U.S. PATENT DOCUMENTS

| | | | |
|---|---|---|---|
| 3,645,835 | 4/1972 | Hodgson | 128/156 |
| 3,888,247 | 6/1975 | Stenvall | 128/156 |
| 4,231,357 | 11/1980 | Hessner | 128/156 |
| 4,340,043 | 7/1982 | Seymour | 128/156 |

OTHER PUBLICATIONS

REVCO, Non-Adherent Sterile Pad, Distributed by Revco D.S., Inc., Twinsburg, Ohio.
Curity "Telfa", Ouchless Sterile Pad, distributed by Colgate-Palmolive Co., New York, N.Y.
Johnson & Johnson, "Steri-Pad" for general bandaging and wound cleansing, distributed by Johnson & Johnson, Inc., New Brunswick, N.J.
Johnson & Johnson, "Adaptic" non-adhering dressing, distributed by Johnson & Johnson, Inc., New Brunswick, N.J.
Spenco, "Dermal Pads" artificial fat tissue for pinpoint protection from skin destruction, distributed by Spenco Medical Corp., Waco, Tex.
Brochure, "Metalline Compresses," Lohmann GmbH & Co. KG, dated 1983.
Advertisement, "Mediskin+Silver," Genetic Laboratories, Inc.
Brochure, "Vigilon" Primary Wound Dressing, Bard Home Health Division, Berkeley Heights, N.J.
Brochure, "Biobrane" a Biocomposite Wound Dressing, Woodroof Manufacturing, Inc., Santa Ana, Calif.
Brochure, Chesebrough-Pond's Non-Adhering Dressings, Chesebrough-Pond's, Inc., Greenwich, Conn.
Brochure, Consider the Base, May 1976, Eaton Laboratories, Norwich, N.Y.
H. Humit, et al., "The Use of Nylon Net in the Management of Skin Grafts Applied to Burn Wounds," 143 Surgery 809–810 (1976).

Primary Examiner—C. Fred Rosenbaum
Assistant Examiner—Sherri E. Vinyard
Attorney, Agent, or Firm—Richards, Harris, Medlock & Andrews

[57] ABSTRACT

A method for dressing wounds to prevent adherence of the covering dressing to the wound includes applying a surfacing barrier (20) as an interpositional material between the wound and covering dressing. The barrier is an extruded, nonwoven polymeric material permeable to blood and serum and having an air permeability between about 300 and about 1140 ft.$^3$/min./ft.$^2$ and a thickness of between about 0.5 mils to about 3.0 mils. The barrier is positioned over the wound and surrounding area and conformed to the shape of the body being treated. The covering dressing is then applied over the barrier.

26 Claims, 6 Drawing Figures

METHOD OF DRESSING WOUNDS

This is a continuation of application Ser. No. 352,117 filed Feb. 25, 1982, now abandoned.

TECHNICAL FIELD

The present invention is directed to a method for dressing wounds or skin grafts using a surfacing barrier between the wound or skin grafts and a covering dressing to eliminate adherence of the dressing to the wound or skin graft. The surfacing barrier is a nonabsorbent extruded polymer or polymer blend in sheet form which is permeable, highly comformable and substantially nonadherent.

BACKGROUND OF THE INVENTION

Use of covering dressings over wounds offers many advantages. However, a major disadvantage is the adherence of the dressing to the wound due to blood, serum or granulation tissue. The adherence of covering dressings to the wound introduces significant problems associated with a dressing change. These problems include pain and discomfort to the patient, disruption of the ongoing healing process or even the "take" on skin grafts, the loss of time resulting from the necessarily slow process of carefully removing the dressing so as not to disrupt the wound and reluctance on the part of the physician to examine a wound early for fear of disrupting the wound or graft.

Numerous types of covering dressings are available; however, the problem with dressing adherence is universal. Historically, efforts have been made to avoid adherence by interposing a dressing between the wound or graft and the absorbent or antibiotic covering dressing. Materials ranging from wedding veils to aluminum foil have been tried. Nonporous films have been used, and various nonadherent materials have been incorporated into the covering dressing to minimize adherence. These materials and treatments of the covering dressings have resulted in little success in avoiding adherence. Indeed, in some cases, the unavailability of a completely nonadherent dressing dictates that no dressing be applied to the wound even through the application of a covering would otherwise be beneficial.

Thus, a critical need exists, and has existed for some time, for a method of wound treatment which eliminates adherence between the covering dressing and the wound.

SUMMARY OF THE INVENTION

The present invention discloses a method for treating open wounds or skin grafts using a surfacing barrier between the wound or graft and the covering dressing to prevent adherence of the dressing to the wound or graft. In the primary embodiment of the invention, the surfacing barrier consists of a synthetic polymer or polymer blend material. Suitable polymer blends, for instance, are polyolefins such as high density polyethylene, polypropylene, or copolymers thereof, blended with a minor proportion of a polymer containing an aryl group such as high impact polystyrene. The barrier may be described as a netted material integrally formed in a synthetic polymeric material by extrusion. The sufacing barrier is nonwoven and nonabsorbent. The barrier is applied to the wound or graft and surrounding area without a backing layer of material attached thereto. The material is highly conformable to the irregular contour of the body part being treated and has an embossed pattern to provide a permeability to facilitate drainage to an absorbent covering dressing applied over the barrier.

In the preferred embodiment, the extruded nonabsorbent material has a thickness of between about 0.5 mils and about 3.0 mils, and has air permeability between about 300 and about 1140 ft.$^3$/min./ft.$^2$. The sheet material has a tensile strength between about 14 and 77 pounds per inch in the roll direction and between about 1.5 and 4.5 pounds per inch in the cross direction.

The use of an extruded barrier sheet of the type described in the method of the present invention provides a material which is highly conformable to irregular contours being treated, provides for drainage of blood and serum, as well as the application of antimicrobial agents which are applied either directly to the surfacing barrier or to the dressing positioned over the barrier. The material, being a nonwoven, polymer or polymer blend sheet formed by extrusion, provides an exceptional nonadherence quality which virtually eliminates adherence of the covering dressing to the wound or graft. This feature minimizes disruption of the graft or wound upon examination or dressing changes and permits such examinations or dressing changes to be made expeditiously and painlessly. Further, the fine mesh configuration of the sheet minimizes the amount of dead space in which bacteria can proliferate.

BRIEF DESCRIPTION OF THE DRAWINGS

For a more complete understanding of the present invention, and for further details and advantages thereof, reference is now made to the following description taken in conjunction with the accompanying drawings, in which.

DESCRIPTION OF THE PREFERRED EMBODIMENTS

Wound dressings facilitate healing in a number of ways. The dressing provides both protection to the wound and a means of absorbing blood and serum from the wound. When a topical antimicrobial agent must be applied to the wound, application is facilitated by the use of a dressing. While there are numerous types of dressings available, the problem of dressing adherence to the wound is universal. Previous efforts to find an interpositional dressing which minimizes adherence have failed to provide a material which is nonadherent, lightweight and highly conformable to the body shape while at the same time having characteristics to allow proper drainage of blood and serum and be nonallergenic and nonreactive. The present invention is directed to a method for dressing a wound or graft which incorporates a nonadherent material which overcomes these deficiencies.

The material used in the present method is easily drapable to the contour of a wound having an irregular shape, and allows drainage of blood and serum so that the overlying absorbent dressing will perform satisfactorily. The material is hypoallergenic and nontoxic to the open or closed wound and, most importantly, nonadherent in every respect to wounds, grafts, body fluids and whatever dressing is used. The material is easily adaptable to any dressing method and procedure which has been or may be used in the future.

Figure 1:
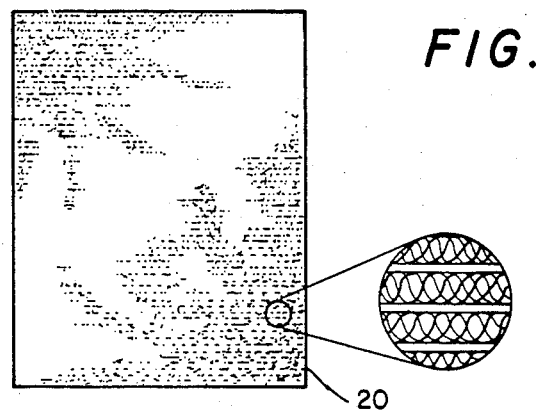
FIG. 1 is a plan view of the surfacing barrier used in the method of the present invention with a portion thereof exploded to show the surfacing barrier in greater detail.

The method incorporates interpositional surfacing barrier 20, shown in FIG. 1, consisting of an extruded, nonwoven, synthetic polymeric material. A polymer blend may be used, for example, including polyolefins such as high density polyethylene, polypropylene, or copolymers thereof, blended, for example, with a polymer containing an aryl group such as high impact polystyrene. Barrier 20 may be of the type described in U.S. Pat. No. 4,135,021, to Patchell et al., issued July 16, 1979, which patent is incorproated herein by reference.

Barrier 20 does not include a backing layer of material attached thereto. Barrier 20 is permeable to blood and serum and has an air permeability between about 300 and about 1140 ft.$^3$/min./ft.$^2$. The thickness of barrier 20 is between about 0.5 mils and about 3.0 mils. Barrier 20 is embossed with a specific geometric pattern and has a tensile strength between about 4 and 77 pounds per inch in the roll direction and between about 1.5 and 4.5 pounds per inch in the cross direction. In FIG. 1, the roll direction is aligned horizontally with the cross direction being perpendicular thereto. The material marketed under the trademark "Delnet" by Hercules, Inc., of Wilmington, Del., having the properties described above, has been found to function successfully in the method of the present invention.

Figure 2:
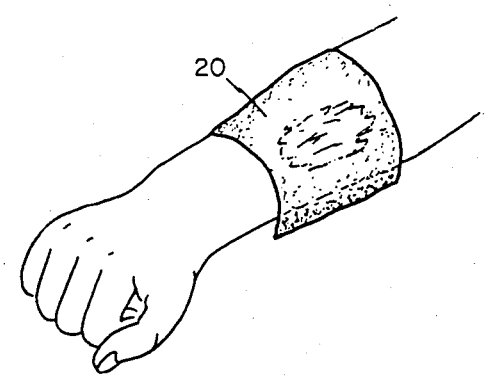
FIG. 2 illustrates the surface barrier being applied to a wound.
Figure 3:
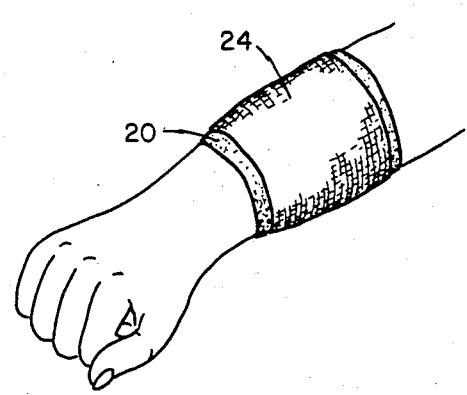
FIG. 3 shows the successive step of an absorbent bandage applied over the surfacing barrier after it has been applied to the wound.

Barrier 20 described has the ability to readily conform, when applied without a backing layer laminated thereto, to the body area treated. In the present method, as is shown in FIG. 2, barrier 20 is placed directly over the wound and surrounding area. It is conformed to the contour of the area on which it is applied. As is shown in FIG. 3, a covering bandage such as an absorbent material 24 is applied over barrier 20 and affixed thereto by a suitable adhesive bandage. Being applied directly to the wound or graft without any backing attached thereto, barrier 20 provides an ideal layer between the wound or graft and cover dressing. An appropriate antimicrobial agent may be applied to the absorbent material 24 for treatment of the wound as desired.

Because barrier 20 is used without a backing layer laminated thereto, it permits the application of an appropriate covering dressing of a selected thickness. Thus, the physician may select the thickness of the covering layer to be applied depending upon the particular wound or body area being treated.

Alternatively, the barrier 20 may be applied without the use of an abosrbent material 24 thereover. For example, where it is desired that a wound not be immediately dressed, barrier 20 may be used to prevent nonadherence to bed clothing. In yet another embodiment of the invention, barrier 20 may be treated with an antimicrobial agent to aid in the control or prevention of infection. In this embodiment, the antimicrobial agent of a suitable nature is impregnated into barrier 20 during or after manufacture.

Because of its composition as an extruded, nonwoven polymer or polymer blend material, interpositional barrier 20 is nonadherent in every repect to wounds, grafts or body fluids. Further, being applied directly to the wound without any backing attached thereto, barrier 20 provides an ideal layer which can be used on any wound, particularly burn wounds which may encompass large parts of the body. Barrier 20 is highly conformable and thus will easily conform to irregular contours, such as, for example, when injury or operations expose vital organs, bones or muscle tissue. Barrier 20 has been found to provide sufficient drainage so that the overlying absorbent dressing will perform satisfactorily. It is nonallergenic and nonreactive to the open or closed wound. Further, surfacing barrier 20 is lightweight and easily drapable to conform to irregular body shapes. Most important, however, is the exceptional nonadherent quality of the barrier 20 which, when used as taught by the invention, virtually eliminates adherence of absorbent material 24 to the wound or graft. The fine mesh configuration of barrier 20 minimizes the amount of space in which bacteria can proliferate. Also, the interpositional barrier is adaptable to any dressing technique or system used or likely to be used.

In view of the virtual elimination of adherence of the covering dressing 24 to the wound, the present invention provides the very real possibility that dressing removal and changes be conducted by the patient or by another not specifically skilled in this area. Thus, frequent changes of bandages are greatly facilitated, readily improving the healing process.

Although barrier 20 has been illustrated and described in FIGS. 1–3 as being applied as the contact layer directly to the wound or skin graft, it will be understood that barrier 20 may at times be applied over a fine mesh gauze which is applied initially as the contact layer to the wound or skin graft. For example, when treating the donor site in a skin graft operation, a fine mesh gauze may be applied as the contact layer, with barrier 20 and a covering dressing 24 applied thereover. In other cases, barrier 20 may be substituted for the fine mesh gauze and serve as the contact layer. In many cases, this substitution will be advantageous in that bacteriologic studies have shown that bacteria will proliferate within the interstices of the polyfilament cotton network of fine mesh gauze. In contrast, barrier 20, being a nonwoven polymer material, minimizes bacteria growth potential.

Figure 4:
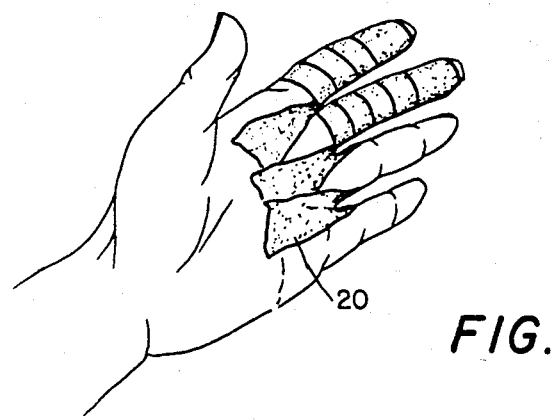
FIGS. 4, 5 and 6 show the use of the method of the present invention to dress a wound on the hand and fingers.
Figure 5:
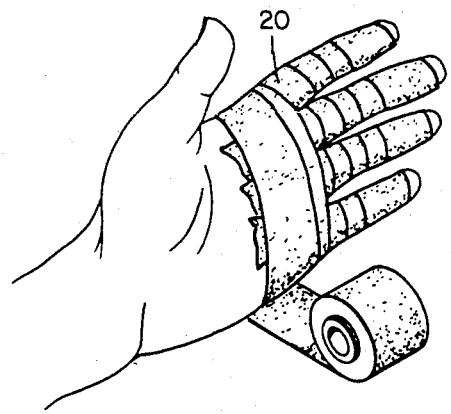
Figure 6:
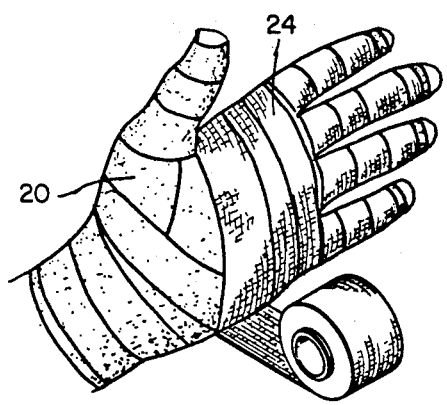

While barrier 20 may substitute as the dressing contact layer, its primary advantage is in preventing adherence between the wound or skin graft and the covering dressing 24. At the same time, barrier 20 is extremely flexible, and thus permits the physician to easily conform barrier 20 to irregular contours of body areas being treated. This advantage is illustrated in FIGS. 4, 5 and 6 wherein the use of barrier 20 is applied to a wound on the hands and fingers. As is shown in FIG. 4, appropriate pieces of barrier so may first be engaged to the irregular wound areas, such as between and around the fingers. Because barrier 20 is highly conformable and is used without a backing layer attached thereto, it may be easily applied to the irregular contoured areas. Following the application of barrier 20 to the wound area, a covering dressing 24 is then applied thereover (FIG. 6). Thus, it can be appreciated that the method of the present invention provides a means for dressing wounds in the most difficult areas to prevent adherence of the covering dressing 24 to the wound.

The method of the present invention also contemplates the application of barrier 20 in large sheet form for overlying large portions of a patient's body so that a covering, such as a sheet or blanket, may be applied thereover. In this arrangement, a large sheet of the barrier 20 is laid over the portion of, or entire body to be covered. This is followed by the placement of a sheet or blanket or other covering over the body or portion thereof. Barrier 20 may be tacked at spaced points to the covering to facilitate its use.

Although preferred embodiments of the invention have been described in the foregoing detailed description and illustrated in the accompanying drawings, it will be understood that the invention is not limited to the embodiments disclosed, but is capable of numerous rearrangements, modifications and substitutions of parts and elements without departing from the spirit of the invention. Accordingly, the present invention is intended to encompass such rearrangements, modifications and substitutions of parts and elements as fall within the spirit and scope of the invention.

I claim:

1. A method of dressing an open wound, burn or skin graft, comprising:
    placing an adhesive-free surfacing barrier without a backing layer and, without any barrier supporting base layer pieces, in direct contact with the wound, burn or graft, said barrier being in direct contact with the surfaces of the body adjacent the wound, burn or graft, said barrier being comformable to the contours of the wound, burn or graft site and the adjacent body surfaces, said barrier consisting of a nonwoven, netted material integrally formed in a synthetic polymeric material and possessing straight smooth parallel longitudinal ribs interconnected by a plurality of fibrillated and split strands exhibiting a plurality of small fibres non-uniformly interspersed with a plurality of differently sized voids and said synthetic polymeric material consisting of a blend of at least two incompatible polymers extruded in sheet form, the blend comprising a mixture of a major proportion by weight of a polyolefin and a minor proportion by weight of a polymer containing an aryl group, said barrier being permeable and nonabsorbent to blood and serum and said barrier being substantially nonadherent to the wound, burn or graft site or adjacent body surfaces; and
    placing an absorbent covering dressing over the surfacing barrier, said covering dressing being of a predetermined thickness to adsorb fluid from the wound, burn or graft whereby traumatic disruption of the graft, burn or wound is minimized upon removable of said covering dressing for visual examinations of the graft, burn or wound or changes of said cover dressing.

2. The method according to claim 1 wherein said polyolefin is selected from the group consisting of polyethylene, polypropylene, and copolymers thereof.

3. The method according to claim 1 wherein said barrier has a thickness between about 0.5 mils and about 3.0 mils.

4. The method according to claim 1 wherein said barrier has an air permeability between about 300 and about 1140 ft.$^3$/min./ft.$^2$.

5. The method according to claim 1 wherein the barrier has a tensile strength between about 14 and 77 pounds per inch in the roll direction and between about 1.5 and 4.5 pounds per inch in the cross direction.

6. The method according to claim 1 wherein said surfacing barrier is impregnated with an antimicrobial agent.

7. A method of dressing an open wound, burn or skin graft comprising:
    applying a nonwoven, polymeric, adhesive-free barrier material in sheet form, without any backing material or base layer supporting pieces attached thereto, directly onto the wound, burn or graft area and surrounding body surfaces, said sheet material being permeable and nonabsorbent to blood and serum, and substantially non-adherent to the wound, burn or graft site, and having a fine mesh configuration having an air permeability between about 300 to about 1140 ft. $^3$/min./ft.$^2$ to minimize the potential for bacteria growth, and said barrier sheet being a netted material integrally formed in a synthetic polymer material and possessing straight smooth parallel longitudinal ribs interconnected by a plurality of fibrillated and split strands exhibiting a plurality of small fibres non-uniformly interspersed with a plurality of differently sized voids and said synthetic polymeric material consisting of a blend of at least two incompatible polymers extruded in sheet form, the blend comprising a mixture of a major proportion by weight of a polyolefin and a minor proportion by weight of a polymer containing an aryl group;
    positioning said barrier sheet onto the wound, burn or graft and surrounding body surface area to conform said barrier sheet material to the shape of the body area being treated; and
    applying an absorbent dressing over the barrier sheet, said absorbent dressing being of a predetermined thickness to be conformable to the treated body area, whereby traumatic disruption of the graft, burn or wound is minimized upon removal of said absorbent dressing for visual examinations of the wound, burn or graft or changes of said absorbent dressing.

8. The method according to claim 7 wherein said barrier sheet has a thickness of between about 0.5 mils and about 3.0 mils.

9. The method according to claim 7, wherein said barrier sheet has a tensile strength of between about 14 and 77 pounds per inch in the roll direction and between about 1.5 and 4.5 pounds per inch in the cross direction.

10. A method of dressing an open wound, burn or skin graft comprising:
    applying a layer of adhesive-free sheet material directly onto the wound, burn or graft, said material being an extruded, nonwoven material permeable and nonabsorbent to blood and serum and having a thickness of between about 0.5 mils and 3.0 mils and said material being integrally formed in a synthetic polymer material and possessing straight smooth parallel longitudinal ribs interconnected by a plurality of fibrillated and split strands exhibiting a plurality of small fibres non-uniformly interspersed with a plurality of differently sized voids and said synthetic polymeric material consisting of a blend of at least two incompatible polymers, the blend comprising a mixture of a major proportion by weight of a polyolefin and a minor proportion by weight of a polymer containing an aryl group;
    positioning said sheet material over the wound, burn or graft and surrounding area to conform the material to the shape of the body area being treated, said sheet material being positioned without any supporting base layer pieces; and securing an abosorbent dressing over said sheet material after contouring said sheet material to the shape of the body area being treated, said absorbent dressing being of a predetermined thickness to conform to the contours of the body treatment area, whereby traumatic disruption of the graft, burn or wound is minimized upon removal of said absorbent dressing for visual examinations of the wound, burn or graft or changes of said absorbent dressing.

11. The method according to claim 10 wherein said sheet material has an air permeability of from about 300 to about 1140 ft.$^3$/min./ft.$^2$.

12. The method according to claim 10 wherein the sheet material has a tensile strength between about 14 and 77 pounds per inch in the roll direction and between about 1.5 and 4.5 pounds per inch in the cross direction.

13. A method of dressing an open wound, burn or skin graft comprising:

placing an adhesive-free surfacing barrier directly onto the wound, burn or graft, without any supporting base layer, said barrier consisting of a netted material integrally formed in a synthetic polymer material and possessing straight smooth parallel longitudinal ribs interconnected by a plurality of fibrillated and split strands exhibiting a plurality of small fibres non-uniformly interspersed with a plurality of differently sized voids and said synthetic polymeric material consisting of a blend of at least two incompatible polymers extruded in sheet form, the blend comprising a mixture of a major proportion by weight of a polyolefin and a minor proportion by weight of a polymer containing an aryl group, said barrier being nonabsorbent and permeable to blood and serum and without a backing layer of material attached thereto, said barrier being substantially nonadherent to the wound, burn or graft, whereby disruption of the graft, burn or wound is minimized for examinations or dressing changes.

14. The method according to claim 13 wherein the polymer in sheet form includes a polyolefin blended with a polymer containing an aryl group.

15. The method according to claim 13 wherein the surfacing barrier is impregnated with an antimicrobial agent.

16. The method according to claim 13 wherein said barrier has a thickness between about 0.5 mils and about 3.0 mils.

17. A method according to claim 1, where said aryl group polymer is a high impact polystyrene.

18. A method of dressing a donor site, comprising:

applying a sheet of fine mesh gauze directly onto the donor site as a contact layer;

applying an adhesive-free surfacing barrier directly over said sheet of fine mesh gauze without any supporting base layer pieces, said surfacing barrier consisting of a nonwoven, netted synthetic polymer material and possessing straight smooth parallel longitudinal ribs interconnected by a plurality of fibrillated and split strands exhibiting a plurality of small fibres non-uniformly interspersed with a plurality of differently sized voids and said synthetic polymeric material being extruded in sheet form from a blend of at least two incompatible polymers, the blend comprising a mixture of a major proportion by weight of polyolefin and a minor proportion by weight of a polymer containing an aryl group;

said surfacing barrier being nonabsorbent and permeable to blood and serum and being conformable to the donor site and adjacent body area; and applying an absorbent covering dressing over said surfacing barrier, said covering dressing being of a predetermined thickness to conform to the donor site and adjacent body area, whereby disruptions of the donor site are minimized for examinations or dressing changes.

19. The method according to claim 7 wherein said aryl group polymer is a high impact polystyrene.

20. The method according to claim 10 wherein said aryl group polymer is a high impact polystyrene.

21. The method according to claim 13 wherein said aryl group polymer is a high impact polystyrene.

22. A method of dressing a wound, burn or skin graft wherein said wound, burn or skin graft is located substantially about the periphery of a trunk portion of the body, comprising:

placing an adhesive-free surfacing barrier directly onto the wound, burn or graft, without any supporting base layer pieces, said surfacing barrier being placed completely about the periphery of the body trunk portion upon which the wound, burn or graft is located, said surfacing barrier consisting of a netted material integrally formed in a synthetic polymer material and possessing straight smooth parallel longitudinal ribs interconnected by a plurality of fibrillated and split strands exhibiting a plurality of small fibres non-uniformly interspersed with a plurality of differently sized voids and said synthetic polymeric material consisting of a blend of at least two incompatible polymers, the blend comprising a mixture of a major proportion by weight of a polyolefin and a minor proportion by weight of a polymer containing an aryl group, said barrier being substantially nonabsorbent and permeable to blood and serum and without a backing layer of material attached thereto, whereby disruption of the graft, burn or wound is minimized for examination of the graft, burn or wound or dressing changes.

23. The method according to claim 22 wherein said polyolefin is selected from the group consisting of polyethylene, polypropylene and co-polymers thereof.

24. The method according to claim 22 wherein said aryl group polymer is a high impact polystyrene.

25. The method according to claim 22, further comprising:

placing an absorbent covering dressing over the surfacing barrier, said covering dressing being of a predetermined thickness to absorb fluid from the wound, burn or graft and to conform to the contours of the wound, burn or graft site and adjacent body surfaces.

26. The method according to claim 13 wherein said polyolefin is selected from the group consisting of polyethylene, polypropylene and co-polymers thereof.

* * * * *